United States Patent
Gross et al.

(10) Patent No.: US 8,277,517 B2
(45) Date of Patent: Oct. 2, 2012

(54) LIGHTENING AGENT HAVING CATIONIC ACYLPYRIDINIUM DERIVATIVES AND CERTAIN AMINO ACIDS

(75) Inventors: Wibke Gross, Hueckelhoven (DE); Ralph Nemitz, Juechen (DE); Astrid Kroos, Monheim (DE); Georg Knuebel, Dusseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/445,412

(22) Filed: Apr. 12, 2012

(65) Prior Publication Data

US 2012/0192891 A1     Aug. 2, 2012

Related U.S. Application Data

(63) Continuation of application No. PCT/EP2010/063398, filed on Sep. 13, 2010.

(30) Foreign Application Priority Data

Oct. 13, 2009  (DE) .......................... 10 2009 045 631

(51) Int. Cl.
*D06L 3/00* (2006.01)
(52) U.S. Cl. ................... 8/101; 8/107; 8/109; 8/111
(58) Field of Classification Search .............. 8/101, 107, 8/109, 111
See application file for complete search history.

(56) References Cited

U.S. PATENT DOCUMENTS

| 6,129,770 A | 10/2000 | Deutz et al. |
| 8,034,122 B2 * | 10/2011 | Gross et al. ........................ 8/101 |
| 2005/0262647 A1 | 12/2005 | Hoeffkes et al. |

FOREIGN PATENT DOCUMENTS

| DE | 10148845 A1 | 4/2003 |
| DE | 102005062360 A1 | 6/2007 |
| DE | 102007047685 A1 | 7/2008 |
| EP | 1800654 A2 | 6/2007 |

* cited by examiner

*Primary Examiner* — Eisa Elhilo

(57) ABSTRACT

Method for lightening keratinous fibers, wherein a cosmetic carrier comprises (i) at least one oxidation agent, (ii) at least one acylpyridinium derivative of formula (I) and (iii) at least one amino acid comprising hydroxyl groups and/or the physiologically compatible salts thereof and/or the alkyl esters thereof.

12 Claims, No Drawings

LIGHTENING AGENT HAVING CATIONIC ACYLPYRIDINIUM DERIVATIVES AND CERTAIN AMINO ACIDS

CROSS REFERENCE TO RELATED APPLICATIONS

The present application is a continuation of International Patent Application No. PCT/EP2010/063398 filed 13 Sep. 2010, which claims priority to German Patent Application No. 10 2009 045 631.7 filed 13 Oct. 2009, both of which are incorporated herein by reference.

The present invention relates to agents for use on keratinic fibers, particularly human hair, and in particular to agents for lightening keratinic fibers comprising cationic acylpyridinium derivatives, certain amino acids or salts or esters thereof and an oxidizing agent, as well as a corresponding method.

Many consumers desire to lighten their own hair, as blond hair color is considered to be attractive and worthwhile from a fashion point of view. Various blonding agents with different blonding power are commercially available for this purpose. Oxidizing agents present in these products are capable of lightening the hair fibers by oxidatively degrading the hair's own colorant, melanin.

Use of hydrogen peroxide—optionally with ammonia or other alkalizing agents—as the sole oxidizing agent suffices for a moderate blonding effect; however, for an intensive blonding effect a mixture of hydrogen peroxide and peroxydisulfate salts and/or peroxymonosulfate salts is typically used. However, lightening of the hair is also accompanied by damage to the hair, as not only the hair colorant but also other structural constituents of the hair are oxidatively degraded. Depending on the intensity of the degree of damage, this manifests itself as rough, brittle and difficultly combable hair, a reduced resistance and tensile strength of the hair and even breakage of the hair. In general, the greater the amount of added hydrogen peroxide and optional peroxydisulfates, the greater will be the damage caused to the keratinic fibers. Hair dyes or lighteners having a good lightening power without concomitantly damaging the hair fiber are unknown as yet.

Even if blonding agents that are currently commercially available generally have good lightening powers, they cannot be considered optimal due to damage to the hair, long application times and the potential skin irritation from the high concentrations of oxidizing and alkalizing agents.

Accordingly, the present invention provides novel agents for lightening or blonding hair which meet or exceed the lightening power of common commercially available agents, but do not exhibit the abovementioned disadvantages and in particular cause less damage to the hair.

DE 102007047685 A1 discloses that certain cationic 4-acetylpyridinium derivatives and certain imidazole derivatives are capable of acting as an activator for hydrogen peroxide and thereby achieve an improved lightening effect on hair versus use of the oxidizing agent alone. In this context, a derivative of imidazole, particularly imidazole itself, was cited as the co-activator. On toxicological grounds, use of imidazole is no longer indicated and the search for an efficient substitute is a further central object of this invention.

It has now been found in a completely unpredictable manner that a specific combination of an inventive pyridinium derivative of the general structure (I), a hydroxyl group-containing amino acid and/or its physiologically acceptable salts or alkyl esters as the specific co-activator and an oxidizing agent provides a bleaching effect that meets or exceeds the prior art, and lightens the hair much more than would be possible by addition of a comparable amount of hydrogen peroxide alone.

Use of cationic acylpyridinium derivatives in hair dyeing is known, for example, from DE 10148845 A1 or DE 10261656 A1. However, these derivatives in both documents are described together with at least one second dyeing component as the dyeing agent and thus for increasing the color intensity of the hair. From the prior art, it is not at all evident that these acylpyridinium derivatives can be used with a very good decolorization power for lightening hair.

Because of the improved blonding power when using the inventive agent, the amount of added oxidizing agent can be reduced, thereby minimizing damage to the hair. In this way, the contact time required to achieve a lightening effect comparable with the prior art can also be diminished.

The inventive agents oxidatively decolorize the natural dye melanin. In the absence of additional dyes/dye precursors, the inventive combination of active substances does not visibly form any dye in the keratin-containing fiber. Synthetic dyes previously present on or in the keratinic fiber can also be bleached with the help of the inventive agent.

Accordingly, a first subject matter of the present invention is an agent for treating keratinic fibers, particularly human hair, comprising in a cosmetic carrier
(i) at least one oxidizing agent,
(ii) at least one acylpyridinium derivative of Formula (I)

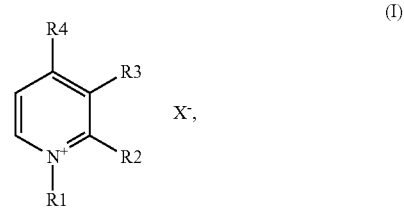

wherein
R1 is a $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a carboxy $C_1$-$C_6$ alkyl group, an aryl $C_1$-$C_6$ alkyl group, a heteroaryl $C_1$-$C_6$ alkyl group, an aryl group or a heteroaryl group,
R2, R3 and R4 each independently of one another is hydrogen, a $C_1$-$C_6$ alkyl group, a halogen atom or a $C_1$-$C_6$ acyl group, with the proviso that at least one of the R2, R3 and R4 groups is a $C_1$-$C_6$ acyl group, and
$X^-$ is a physiologically acceptable anion, and
(iii) at least one hydroxyl group-containing amino acid and/or its physiologically acceptable salts and/or its alkyl esters.

Keratinic or keratin fibers are understood here to mean furs, wool, feathers and particularly human hair. Although agents according to the invention are primarily suitable for dyeing and/or lightening keratin fibers, in principle, nothing prevents their use in other fields.

Agents according to the invention comprise the active substances in a cosmetic carrier. The cosmetic carrier is preferably aqueous, alcoholic or aqueous-alcoholic. For the purpose of bleaching the hair, such carriers include creams, emulsions, gels or also surfactant-containing foaming solutions such as shampoos, foam aerosols or other preparations suitable for use on the hair. However, for storage, it is also possible to provide a formulation that is in powder form or even in tablet form, which is preferred for lighteners. Prior to use, this is diluted in a solvent, such as water or with organic solvents or with aqueous organic solvent mixtures to obtain the ready for use mixture. In the context of the invention, an aqueous carrier comprises at least 40 wt %, especially at least 50 wt % water. For the purposes of the present invention, aqueous-alcoholic carriers are understood to mean water-containing solutions comprising 3 to 70% by weight of a $C_1$-$C_4$ alcohol, particularly ethanol or isopropanol. The agents can additionally contain further organic solvents such as methoxybutanol, ethyl diglycol, 1,2-propylene glycol, n-propanol, n-butanol, n-butylene glycol, glycerin, diethylene glycol monoethyl ether, and diethylene glycol mono-n-butyl ether. Preference here is given to all water-soluble organic solvents. Preferred inventive agents additionally comprise a non-aqueous solvent, wherein particularly preferred inventive agents comprise the solvent in a concentration of 0.1 to 30 wt %, preferably in a concentration of 1 to 20 wt %, quite particularly preferably in a concentration of 2 to 10 wt %, relative to the agent.

The inventive agent contains at least one oxidizing agent as the first essential constituent. All established oxidizing agents can be used as the oxidizing agent. Hydrogen peroxide as well as suitable perborate, peroxide, persulfate or organic peracid salts of alkali metals, alkaline earth metals, iron, aluminum or zinc can be used. In one embodiment, the agent comprises at least one compound as the oxidizing agent chosen from hydrogen peroxide, alkali metal peroxides and/or alkali metal perborates. These include sodium peroxide, potassium peroxide, sodium perborate and potassium perborate. Preferably hydrogen peroxide itself is used as an aqueous solution. However, hydrogen peroxide can also be added in the form of a solid addition compound of hydrogen peroxide onto inorganic or organic compounds, such as sodium percarbamide, polyvinyl pyrrolidone $nH_2O_2$ (n is a positive integer greater than 0), urea peroxide and melamin peroxide. Preferred oxidizing agents are chosen from hydrogen peroxide, sodium peroxide and sodium perborate, particularly from hydrogen peroxide.

The mixture preferably comprises 0.01 to 25 wt %, more preferably 0.1 to 15 wt % and particularly preferably 0.5 to 8 wt % of the oxidizing agents, based on total weight of the ready for use agent.

The inventive agent further contains at least one compound according to Formula (I). Non-limiting examples for the cited substituents of the compounds of Formula (I) are as follows: Exemplary $C_1$-$C_6$ alkyl groups are the groups —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$. Examples for a $C_2$-$C_6$ alkenyl group are a prop-2-enyl group (allyl group), a 2-methyl-prop-2-enyl group, a but-3-enyl group, a but-2-enyl group, a pent-4-enyl group or a pent-3-enyl group, wherein the prop-2-enyl group is preferred. Exemplary $C_1$-$C_6$ hydroxyalkyl groups are —$CH_2OH$, —$CH_2CH_2OH$, —$CH_2CH_2CH_2OH$, —$CH_2CH(OH)CH_3$ and —$CH_2CH_2CH_2CH_2OH$, the —$CH_2CH_2OH$ group being preferred. Exemplary $C_1$-$C_6$ alkoxy $C_2$-$C_6$ alkyl groups are the groups —$CH_2CH_2OCH_3$, —$CH_2CH_2CH_2OCH_3$, —$CH_2CH_2OCH_2CH_3$, —$CH_2CH_2CH_2OCH_2CH_3$, —$CH_2CH_2OCH(CH_3)_2$, —$CH_2CH_2CH_2OCH(CH_3)_2$ groups. Exemplary carboxy $C_1$-$C_6$ alkyl groups are the carboxymethyl group, the 2-carboxyethyl group or the 3-carboxypropyl group. Exemplary aryl $C_1$-$C_6$ alkyl groups are the benzyl group and the 2-phenylethyl group. Exemplary heteroaryl $C_1$-$C_6$ alkyl groups are the pyridin-2-ylmethyl group, the pyridin-3-ylmethyl group, the pyridin-4-ylmethyl group, the pyrimidin-2-ylmethyl group, the pyrrol-1-ylmethyl group, the pyrrol-1-ylethyl group, the pyrazol-1-ylmethyl group or the pyrazol-1-ylethyl group Exemplary aryl groups are the phenyl group, the 1-naphthyl group or the 2-naphthyl group. Exemplary heteroaryl groups are the pyridin-2-yl group, the pyridin-3-yl group, the pyridin-4-yl group, the pyrimidin-2-yl group, the pyrrol-1-yl group, the pyrrol-2-yl group, the pyrazol-1-yl group or the pyrazol-3-yl group or the pyrazol-4-yl group. Exemplary $C_1$-$C_6$ acyl groups are acetyl (1-oxo-ethyl), 1-oxo-propyl, 1-oxo-butyl, 1-oxo-pentyl, 1-oxo-2,2-dimethylpropyl and 1-oxo-hexyl groups.

In one embodiment of the present invention, those compounds according to Formula (I) are preferred wherein R1 of the general structure (I) is a $C_1$-$C_6$ alkyl group, a $C_2$-$C_6$ alkenyl group or a $C_2$-$C_6$ hydroxyalkyl group. It is inventively preferred when R1 is a $C_1$-$C_6$ alkyl group, preferably methyl, ethyl, n-propyl or isopropyl, and particularly preferably methyl.

It has been shown that acylpyridinium derivatives according to Formula (I) inventively possess particularly advantageous properties when they carry the acyl group in either the 2- or 4-position on the pyridine ring. Preferred compounds of Formula (I) are also those compounds in which either R2 or R4 is a $C_1$-$C_6$ acyl group, preferably an acetyl group. It is further preferred when one of R2 or R4 is an acetyl group, whereas the other as well as R3 are each hydrogen. Accordingly another embodiment of the present invention is one wherein the agent comprises at least one 2-acetylpyridinium derivative and/or 4-acetylpyridinium derivative as the acylpyridinium derivative according to Formula (I).

In this regard, suitable acetylpyridinium derivatives are the physiologically acceptable salts that as the cation comprise an acetylpyridinium derivative chosen from 4-acetyl-1-methylpyridinium, 4-acetyl-1-allyl-pyridiniunn, 4-acetyl-1-(2-hydroxyethyl)pyridinium, 2-acetyl-1-methylpyridinium, 2-acetyl-1-allyl-pyridinium and 2-acetyl-1-(2-hydroxyethyl)pyridinium.

Anion $X^-$ according to Formula (I) is preferably chosen from halide, particularly chloride, bromide and iodide, benzene sulfonate, p-toluene sulfonate, $C_1$-$C_4$-alkylsulfonate, trifluoromethane sulfonate, acetate, trifluoroacetate, perchlorate, sulfate, hydrogen sulfate, tetrafluoroborate, hexafluorophosphate or tetrachlorozincate. It is inventively particularly favored when the anion $X^-$ is hydrogen sulfate, p-toluene sulfonate, benzene sulfonate or acetate.

Those agents are inventively particularly preferred when the acylpyridinium derivative according to Formula (I) is chosen from 4-acetyl-1-methylpyridinium p-toluene sulfonate, 4-acetyl-1-methylpyridinium benzene sulfonate, 4-acetyl-1-methylpyridinium hydrogen sulfate, 4-acetyl-1-methylpyridinium acetate, 4-acetyl-1-allylpyridinium p-toluene sulfonate, 4-acetyl-1-allylpyridinium benzene sulfonate, 4-acetyl-1-allylpyridinium hydrogen sulfate, 4-acetyl-1-allylpyridinium acetate, 2-acetyl-1-methylpyridinium p-toluene sulfonate, 2-acetyl-1-methylpyridinium benzene sulfonate, 2-acetyl-1-methylpyridinium hydrogen sulfate, 2-acetyl-1-methylpyridinium acetate, 2-acetyl-1-allylpyridinium p-toluene sulfonate, 2-acetyl-1-allylpyridinium benzene sulfonate, 2-acetyl-1-allylpyridinium hydrogen sulfate and 2-acetyl-1-allylpyridinium acetate.

Inventively preferred agents contain a compound chosen from 4-acetyl-1-methylpyridinium p-toluene sulfonate and/or 2-acetyl-1-methylpyridinium p-toluene sulfonate, particularly 4-acetyl-1-methylpyridinium p-toluene sulfonate, as the acylpyridinium derivative according to Formula (I).

Preferred agents comprise one or more of the acylpyridinium derivative(s) of Formula (I) in an amount of 0.001 to 15 wt %, preferably 0.01 to 10 wt % and particularly preferably 0.1 to 5 wt %, based on total weight of the ready for use mixture.

As the third essential constituent, the inventive agent contains at least one hydroxyl group-containing amino acid and/or its physiologically acceptable salts and/or its alkyl esters.

In the context of the invention, an amino acid is an organic compound having in its structure at least one protonizable amino group and at least one carboxylic acid (—COOH) group or a sulfonic acid (—$SO_3H$) group. Preferred amino acids are amino carboxylic acids, particularly α-amino carboxylic acids and ω-amino carboxylic acids, with α-amino carboxylic acids being particularly preferred.

α-Amino carboxylic acids usually contain at least one asymmetric carbon atom. For the nomenclature of enantiomers, the absolute configuration of these centers of chirality can be determined with the help of the Cahn-Ingold-Prelog rules, and the enantiomers are described by the stereodescriptors R and S. On historical grounds, the D/L convention can also be used to describe amino acids. In the context of the present invention, both possible enantiomers can be equally used as the specific compound or also mixtures thereof, particularly as the racemates. In the course of the actual invention, both enantiomers are included in the invention—both the R-enantiomers and the S-enantiomers of each substance are in accordance with the invention. Moreover, an equimolar mixture of both enantiomers (racemate) as well as every other conceivable molar ratio of R- to S-enantiomer can be employed in the agents for lightening hair. However, it is particularly advantageous to employ the naturally occurring preferred isomeric form, mainly in the L-configuration.

In the context of the invention, a hydroxyl group-containing amino acid is an organic compound having in its structure at least one protonizable amino group and at least one carboxylic acid group or a sulfonic acid group as well as at least one hydroxyl group. The hydroxyl group is preferably bonded to an aliphatic group.

The hydroxyl group-containing amino acid is preferably added in free form to the inventive agents. In a number of cases, however, it is also advantageous to incorporate the amino acids in salt form. Preferred salts include in particular hydrochlorides, hydrobromides and sulfates. In the scope of the present invention, alkyl esters of the physiologically acceptable amino acids refer to those compounds in which an ester group is formed from the carboxylic acid group or the sulfonic acid group with an alkyl group, particularly a $C_1$-$C_6$ alkyl group. The methyl or ethyl ester of the amino acid is particularly preferred.

Another embodiment of the inventive use is wherein the agent contains as the hydroxyl group-containing amino acid at least one compound chosen from the group serine, tyrosine, threonine, 4-hydroxyproline and/or methyl or ethyl esters and/or physiologically acceptable salts thereof.

The hydroxyl group-containing amino acid is particularly preferably at least one compound chosen from L-serine ((S)-2-amino-3-hydroxypropionic acid), D-serine ((R)-2-amino-3-hydroxypropionic acid), D-/L-serine ((R/S)-2-amino-3-hydroxypropionic acid), L-serine methyl ester(methyl(S)-2-amino-3-hydroxypropanoate), D-serine methyl ester(methyl(R)-2-amino-3-hydroxypropanoate), D-/L-serine methyl ester(methyl(R/S)-2-amino-3-hydroxypropanoate, L-serine ethyl ester(ethyl(S)-2-amino-3-hydroxypropanoate), D-serine ethyl ester(ethyl(R)-2-amino-3-hydroxypropanoate) and D-serine ethyl ester(ethyl(R/S)-2-amino-3-hydroxypropanoate).

In this regard, agents containing serine for improving the lightening power are inventively particularly preferred. The agent particularly preferably comprises serine, D-serine or D/L-serine; quite particularly preferably, however, L-serine, especially in free form, but also as the hydrochloride.

Another embodiment is one wherein the agent has one or more hydroxyl group-containing amino acids and/or salts and/or alkyl esters in an amount of 0.01 to 10 wt %, particularly 0.01 wt % to 5 wt %, based on total weight of the ready for use agent.

When considering the preceding cited preferred embodiments, there is a quite specific and expressly preferred embodiment when the agent for lightening keratinic fibers comprises in a cosmetic carrier, besides hydrogen peroxide as the first component, a second component chosen from at least one compound of 4-acetyl-1-methylpyridinium p-toluene sulfonate, 4-acetyl-1-methyl-pyridinium benzene sulfonate, 4-acetyl-1-methylpyridinium bromide, 4-acetyl-1-methylpyridinium hydrogen sulfate, 4-acetyl-1-allylpyridinium p-toluene sulfonate, 4-acetyl-1-allylpyridinium benzene sulfonate, 4-acetyl-1-allylpyridinium bromide, 4-acetyl-1-allylpyridinium hydrogen sulfate, 4-acetyl-1-(2-hydroxyethyl) pyridinium p-toluene sulfonate, 4-acetyl-1-(2-hydroxyethyl) pyridinium benzene sulfonate, 4-acetyl-1-(2-hydroxyethyl) pyridinium bromide and 4-acetyl-1-(2-hydroxyethyl) pyridinium hydrogen sulfate and 4-acetyl-1-methylpyridinium p-toluene sulfonate as well as from 2-acetyl-1-methylpyridinium benzene sulfonate, 2-acetyl-1-methylpyridinium bromide, 2-acetyl-1-methyl-pyridinium hydrogen sulfate, 2-acetyl-1-allylpyridinium p-toluene sulfonate, 2-acetyl-1-allyl-pyridinium benzene sulfonate, 2-acetyl-1-allylpyridinium bromide, 2-acetyl-1-allylpyridinium hydrogen sulfate, 2-acetyl-1-(2-hydroxyethyl)pyridinium p-toluene sulfonate, 2-acetyl-1-(2-hydroxyethyl)-pyridinium benzene sulfonate, 2-acetyl-1-(2-hydroxyethyl) pyridinium bromide and 2-acetyl-1-(2-hydroxyethyl) pyridinium hydrogen sulfate, and a third component that is at least one compound, chosen from serine, tyrosine, threonine, 4-hydroxyproline and/or methyl or ethyl esters or physiologically acceptable salts thereof in the already described preferred weight fractions.

Finally, agents are quite particularly preferred that have one of the following combinations wherein weight contents again refer to total weight of the ready-for-use agent:

Combination (a):
0.1 to 4.0 wt % 4-acetyl-1-methylpyridinium p-toluene sulfonate, 0.1 to 3.0 wt % L-serine and 0.1 to 12.0 wt % hydrogen peroxide.

Combination (b):
0.1 to 4.0 wt % 4-acetyl-1-methylpyridinium p-toluene sulfonate, 0.1 to 3.0 wt % D/L-serine and 0.1 to 12.0 wt % hydrogen peroxide.

Combination (c):
0.1 to 4.0 wt % 2-acetyl-1-methylpyridinium p-toluene sulfonate, 0.1 to 3.0 wt % L-serine and 0.1 to 12.0 wt % hydrogen peroxide.

Combination (d):
0.1 to 4.0 wt % 2-acetyl-1-methylpyridinium p-toluene sulfonate, 0.1 to 3.0 wt % D/L-serine and 0.1 to 12.0 wt % hydrogen peroxide.

Blonding processes on keratin fibers usually occur in an alkaline medium. However, in order to be as gentle as possible with the keratin fibers and also the skin, it is not desirable to adjust the pH to too high a value. It is therefore preferred for the pH of the ready for use agent to be from 7 to 11, particularly 8 to 10.5. In the context of the present invention, pH values refer to those measured at a temperature of 22° C.

One skilled in the art is aware of commonly used acidification and alkalization agents for adjusting the pH. Alkalization agents that can be used for adjusting the pH are typically chosen from ammonia, inorganic salts, especially of the alkali metal and alkaline earth metals, organic alkalization agents, especially amines and basic amino acids. Inventively preferred acidifiers include food acids such as citric acid, acetic acid, malic acid or tartaric acid, as well as diluted mineral acids. Inventively useable inorganic alkalization agents are preferably chosen from sodium hydroxide, potassium hydroxide, calcium hydroxide, barium hydroxide, sodium phosphate, potassium phosphate, sodium silicate, potassium silicate, sodium carbonate and potassium carbonate. Sodium hydroxide and/or potassium hydroxide are particularly preferred. The basic amino acids are preferably chosen from L-arginine, D-arginine, D/L-arginine, L-lysine, D-lysine, D/L-lysine, particularly preferably L-arginine, D-arginine and D/L-arginine. The additional acidifiers and alkalizers are each preferably present in amounts of 0.05 to 15 wt %, particularly 0.5 to 10 wt %, based on total weight of the ready-for-use agent.

Employing only hydrogen peroxide or its addition products on organic or inorganic compounds is often insufficient for strongly lightening very dark hair. In these cases, a combination of hydrogen peroxide and persulfates or peroxydisulfates is generally employed. It has been shown that an increase in lightening power occurs by mixing the acylpyridinium derivative of general structure (I) and hydroxyl group-containing amino acid not only with hydrogen peroxide alone, but also with a combination of hydrogen peroxide and peroxydisulfates.

Consequently, should the consumer desire a very strong blonding, it can be preferred in another embodiment for the keratin fiber lightening agent to additionally comprise at least one inorganic persulfate salt or peroxydisulfate salt besides the cationic acylpyridinium compound of general structure (I), hydroxyl group-containing amino acids and/or salts or alkyl esters and hydrogen peroxide thereof. Preferred peroxydisulfate salts are ammonium peroxydisulfate, potassium peroxydisulfate and sodium peroxydisulfate. The ready-for-use agent can preferably contain peroxydisulfate salts in an amount of 0.1 to 25 wt %, particularly 0.5 to 15 wt %, based on total weight of the ready-to-use agent.

Agents according to the invention can be produced from two or more separately packaged preparations immediately prior to use. This allows for separation of incompatible ingredients in order to avoid premature reaction.

Therefore, a usual way of preparing the agent is to blend immediately before application a first agent having at least one cationic acylpyridinium derivative of the general Formula (I) and a hydroxyl group-containing amino acid and/or its physiologically acceptable salts or alkyl esters with a second agent having the inventive oxidizing agent.

Accordingly, a further subject matter of the present invention is an agent for lightening keratinic fibers, particularly human hair, which is obtained immediately before application onto the hair from a free-flowing preparation (A) having the cationic acylpyridinium derivative of general Formula (I) and a hydroxyl group-containing amino acid and/or its physiologically acceptable salts or alkyl esters, and from an oxidizing agent preparation (B) having at least one oxidizing agent chosen from hydrogen peroxide and/or its addition compounds on inorganic or organic compounds.

The oxidizing agent preparation (B) is preferably an aqueous, free flowing oxidizing agent preparation. In this regard, preferred inventive agents for lightening keratinic fibers are those wherein the free-flowing oxidizing agent preparation (B)—based on its weight—comprises 40 to 90 wt %, preferably 50 to 85 wt %, particularly preferably 55 to 80 wt %, more preferably 60 to 77.5 wt %, and particularly 65 to 75 wt % water.

The peroxydisulfate salts are generally added in the form of an optionally dedusted powder, paste or in the form of a compressed molded body. In order to avoid premature decomposition of the acylpyridinium derivative due to their contact with the persulfates or peroxydisulfates, it is inventively preferred to provide the persulfates or peroxydisulfates as a separately packaged component (C).

Accordingly, an agent consisting of 3 components for lightening human hair is another subject matter of the present invention. This agent is produced immediately before the application onto the hair by thoroughly blending a free-flowing preparation (A) containing the cationic acylpyridinium derivative of general Formula (I) and a hydroxyl group-containing amino acid and/or its physiologically acceptable salts or alkyl esters together with an oxidizing agent preparation (B) comprising at least one oxidizing agent chosen from hydrogen peroxide and/or its addition compounds on inorganic or organic compounds and additionally a third preparation (C) in powder form having at least one inorganic peroxydisulfate salt.

The mixing of the preparations (A) and (B) or optionally preparations (A), (B) and (C) prior to application results in an application mixture that is an agent according to the invention with the three essential ingredients.

In order to further enhance the power of the oxidizing agent preparation, an optionally hydrated $SiO_2$ compound can be additionally added to the inventive preparation. According to the invention it may be preferred to use the optionally hydrated $SiO_2$ compounds in amounts of 0.05% to 15% by weight, particularly preferably in amounts of 0.15% to 10% by weight and quite particularly preferably in amounts of 0.2% to 5% by weight, based on the anhydrous agent according to the invention. The quantitative data here in each case give the content of the $SiO_2$ compounds (without water fraction thereof) in the agents.

With respect to the optionally hydrated $SiO_2$ compounds, the present invention is not in principle subject to any limitations. Preference is given to silicic acids, oligomers and polymers, and salts thereof. Preferred salts are the alkali metal salts, in particular, the potassium and sodium salts. The optionally hydrated $SiO_2$ compounds can be present in various forms. The $SiO_2$ compounds are inventively preferably added in the form of silica gels or as a water glass. Water glasses are inventively particularly preferred. Particularly preferred water-glasses according to the invention are sold under the names Ferrosil® 119, Natronwasserglas 40/42, Portil® A, Portil® AW and Portil® W, and by Akzo under the name Britesil® C20.

In a preferred embodiment, lighteners according to the invention additionally comprise at least one color changing component. The color changing component is chosen in this regard from at least one oxidation dye precursor and/or substantive dye.

In one embodiment of the present invention, the agent comprises at least one oxidation dye precursor and/or substantive dye as the color changing component. In a preferred embodiment, the dyeing preparation comprises at least one oxidation dye precursor as the color changing component.

Dyeing preparations comprise at least one developer component and optionally at least one coupler component as the oxidation dye precursor. Developer components can develop the actual dyes from themselves but preferably with coupler components. Therefore, dyes according to the invention preferably comprise at least one oxidation dye precursor of the developer type and at least one oxidation dye precursor of the coupler type. Developer and coupler components are usually employed in free form. For substances with amino groups, it can however be preferred to employ them in salt form, especially in the form of the hydrochlorides and hydrobromides or sulfates.

Here, developer components and coupler components are generally used in approximately molar amounts relative to one another. Although molar use has also proven to be expedient, a certain excess of individual oxidation dye precursors is not disadvantageous, such that developer components and coupler components may be present in a molar ratio of 1:0.5 to 1:2.

Particularly preferred developer components are chosen from at least one compound from p-phenylenediamine, p-toluoylenediamine, 2-(2-hydroxy-ethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-2-propanol, bis-(2-hydroxy-5-aminophenyl)methane, 1,3-bis-(2,5-diaminophenoxy)-2-propanol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxy-ethyl)phenol and 4-amino-2-(diethylaminomethyl)phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, as well as the physiologically acceptable salts of these compounds. In this regard, quite particularly preferred developer components are p-toluoylenediamine, 2-(2-hydroxyethyl)-p-phenylenediamine, 2-methoxy-methyl-p-phenylenediamine, N-(4-amino-3-methylphenyl)-N-[3-(1H-imidazol-1-yl)propyl]amine, and/or 4,5-diamino-1-(2-hydroxyethyl)pyrazole as well as the physiologically acceptable salts of these compounds. The developer components are preferably used in an amount of 0.0001 to 10 wt %, preferably 0.001 to 5 wt %, based on the ready-for-use agent.

Coupler components alone, in the context of the oxidative dyeing, do not form any significant coloration; rather they always need the presence of developer components. Therefore it is inventively preferred that when using at least one coupler component, at least one developer component is also used. According to the invention, particularly preferred coupler components are chosen from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)-ethanol, 1,3-bis(2,4-diaminophenoxy)propane, 1-methoxy-2-amino-4-(2-hydroxyethylamino)-benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or physiologically acceptable salts thereof. In this regard, resorcinol, 2-methylresorcinol, 5-amino-2-methylphenol, 3-Aminophenol, 2-(2,4-diaminophenoxy)ethanol, 1,3-bis(2,4-diamino-phenoxy)propane, 1-methoxy-2-amino-4-(2'-hydroxyethylamino)benzene, 2-amino-3-hydroxypyridine and 1-naphthol, as well as physiologically acceptable salts are particularly preferred thereof. The coupler components are preferably used in an amount of 0.0001 to 10 wt %, preferably 0.001 to 5 wt %, based on the ready-for-use agent.

The agents can further comprise at least one substantive dye. These are dyes that are directly absorbed onto the hair and do not require any oxidative process to develop the color. Substantive dyes are usually nitrophenylenediamines, nitroaminophenols, azo dyes, anthraquinones or indophenols. Substantive dyes can be classified into anionic, cationic and non-ionic substantive dyes. The substantive dyes are preferably employed in amounts of 0.001 to 20 wt %, particularly 0.05 to 5 wt %, based on total end-use preparation. The total amount of substantive dyes is preferably a maximum of 20 wt %.

Preferred anionic substantive dyestuffs are known compounds with the designations Acid Yellow 1, Acid Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52 and tetrabromophenol blue.

Preferred cationic substantive dyes include cationic triphenylmethane dyes such as Basic Blue 7, Basic Blue 26, Basic Violet 2 and Basic Violet 14, aromatic systems that are substituted with a quaternary nitrogen group such as Basic Yellow 57, Basic Red 76, Basic Blue 99, Basic Brown 16 and Basic Brown 17 and HC Blue 16, as well as Basic Yellow 87, Basic Orange 31 and Basic Red 51.

Preferred non-ionic substantive dyes are HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-di-amino-2-nitrobenzene, 2-amino-4-nitrophenol, 1,4-bis-(2-hydroxyethyl)-amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]-benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol.

It is not required that each of the optionally comprised substantive dyestuffs be pure compounds. In fact, due to manufacturing processes for the individual dyes, minor quantities of other components may be present as long as they have no detrimental influence on the coloration result or that they must be excluded on other grounds (e.g., toxicological).

In addition, naturally occurring dyestuffs may also be added as found, for example, in henna red, henna neutral, henna black, camomile leaves, sandalwood, black tea, alder buckthorn bark, sage, logwood, madder root, cachou, cedar and alkanet root.

According to the invention, an oxidation lightening agent can also be applied to the hair together with a catalyst that activates the oxidation of the dye precursors (e.g., by atmospheric oxygen). Such catalysts include certain enzymes, iodides, quinones or metal ions.

In addition, it has proven advantageous when the lighteners contain at least one stabilizer or complexant. Common, and in the context of the present invention, preferred chelating complexants include polycarboxylic acids, nitrogen-containing mono or polycarboxylic acids, especially ethylenediaminetetraacetic acid (EDTA), ethylenediaminedisuccinic acid (EDDS) and nitrilotriacetic acid (NTA), geminal diphosphonic acids, in particular 1-hydroxyethane-1,1-diphosphonic acid (HEDP), amino phosphonic acids such as ethylenediaminetetra(methylenephosphonic acid) (EDTMP), diethylenetriaminepenta(methylenephosphonic acid) (DTPMP), phosphonopolycarboxylc acids such as 2-phosphonobutane-1,2,4-tricarboxylic acid as well as cyclodextrins, alkali metal stannates (sodium stannate), alkali metal pyrophosphates (tetrasodium pyrophosphate, disodium pyrophosphate), alkali metal phosphates (sodium phosphate), and phosphoric acid. According to the invention, the agents preferably comprise 0.01 to 3 wt %, preferably 0.05 to 1 wt % complexant, each based on total weight of the agent according to the invention.

The inventively useable agents are preferably formulated as free-flowing preparations. These include especially emulsions, suspensions and gels, particularly preferably emulsions. Free-flowing preparations preferably additionally comprise an emulsifier or a surfactant as the surface active substance, wherein surface active substances are designated as surfactants or as emulsifiers depending on their field of application, and are selected from anionic, cationic, zwitterionic, amphoteric and non-ionic surfactants.

Suitable anionic surfactants for the inventive preparations are all anionic surface-active materials suitable for use on the human body. Preferred anionic surfactants are linear and branched fatty acids containing 8 to 30 carbon atoms (soaps), alkyl sulfates, alkyl ether sulfates and polyethoxylated ether carboxylic acids containing 10 to 18 carbon atoms in the alkyl group and up to 12 glycol ether groups in the molecule.

Zwitterionic surfactants are those surface-active compounds that carry at least one quaternary ammonium group and at least one carboxylate, sulfonate or sulfate group in the molecule. Betaines are particularly suitable zwitterionic surfactants. A preferred zwitterionic surfactant is the fatty acid amide derivative, known under the INCI name Cocamidopropyl Betaine.

In another embodiment of the present invention, the agent additionally comprises at least one amphoteric surfactant. Examples of suitable ampholytic surfactants are N-alkylglycines, N-alkylamino propionic acids, N-alkylamino butyric acids, N-alkylimino dipropionic acids, N-hydroxyethyl-N-alkylamidopropylglycine, N-alkyltaurines, N-alkylsarcosines, 2-alkylamino propionic acids and alkylamino acetic acids. Particularly preferred amphoteric surfactants are commercialized under the INCI name Disodium Cocoamphodipropionate with the trade names Miranol C2M SF conc. (Rhodia), Amphoterge K-2 (Lonza) and Monateric CEM-38 (Unichema) and the name Disodium Cocoamphodiacetate with the trade names Dehyton (Cognis), Miranol C2M (Rhodia) and Ampholak XCO 30 (Akzo Nobel).

Alkyl polyglycosides, particularly $C_8$-$C_{22}$ alkyl mono- and alkyl oligo-glycosides and ethoxylated analogs, are suitable as the non-ionic surfactants thereof. Alkylene oxide addition products on saturated, linear fatty alcohols and fatty acids, each with 2 to 30 moles ethylene oxide per mole fatty alcohol or fatty acid, have proved to be additional preferred non-ionic surfactants. Preparations with excellent properties are also obtained when they comprise fatty acid esters of ethoxylated glycerin as the non-ionic surfactant.

According to the invention, cationic surfactants of the type quaternary ammonium compounds, esterquats and amido amines are likewise preferred. Preferred quaternary ammonium compounds are ammonium halides such as alkyltrimethylammonium chlorides, dialkyldimethylammonium chlorides and trialkylmethylammonium chlorides, as well as the imidazolium compounds known under the INCI names Quaternium-27 and Quaternium-83. Quaternized protein hydrolyzates are further inventively useable cationic surfactants. Alkylamido amines are normally manufactured by amidation of natural or synthetic fatty acids and fatty acid fractions with dialkylamino amines (e.g., Tegoamid® S 18 (stearamidopropyldimethylamine)). Preferred esterquats are quaternized ester salts of fatty acids with triethanolamine, quaternized ester salts of fatty acids with diethanolalkylamines and quaternized ester salts of fatty acids with 1,2-dihydroxypropyldialkylamines, such as the commercial products Stepantex®, Dehyquart® and Armocare®.

The anionic, non-ionic, zwitterionic or amphoteric surfactants are present in amounts of 0.1 to 45 wt %, preferably 1 to 30 wt. % and particularly preferably 1 to 15 wt %, based on total amount of the ready-for-use agent. Compositions used according to the invention preferably contain cationic surfactants in amounts of 0.05 to 10 wt %, particularly preferably 0.1 to 5 wt %, based on total composition.

Furthermore, agents according to the invention can contain additional active substances, auxiliaries and additives such as cationic polymers, non-ionic polymers (vinyl pyrrolidinone/vinyl acrylate copolymers, polyvinyl pyrrolidinone, vinyl pyrrolidinone/vinyl acetate copolymers, polyethylene glycols and polysiloxanes); zwitterionic and amphoteric polymers (acrylamidopropyl-trimethyl-ammonium chloride/acrylate copolymers and octylacrylamide/methyl methacrylate/tert-butylaminoethyl methacrylate/2-hydroxypropyl methacrylate copolymers); anionic polymers (polyacrylic acids, crosslinked polyacrylic acids, vinyl acetate/crotonic acid copolymers, vinyl pyrrolidinone/vinyl acrylate copolymers, vinyl acetate/butyl maleate/isobornyl acrylate copolymers, methyl vinyl ether/maleic anhydride copolymers and acrylic acid/ethyl acrylate/N-tert-butylacrylamide terpolymers); thickeners (agar-agar, guar-gum, alginates, xanthan gum, gum arabicum, karaya gum, locust bean flour, linseed gums, dextrans, cellulose derivatives, e.g. methyl cellulose, hydroxyalkyl cellulose and carboxymethyl cellulose, starch fractions and derivatives such as amylose, amylopectin and dextrins, clays such as e.g. bentonite or fully synthetic hydrocolloids such as e.g. polyvinyl alcohol); hair conditioning compounds (phospholipids, for example soya lecithin, egg lecithin, cephalins as well as silicone oils); protein hydrolyzates of vegetal or animal origin (elastin-, collagen-, keratin-, milk albumin-, soya protein- and wheat protein-hydrolyzates, condensation products with fatty acids as well as quaternized protein hydrolyzates thereof); perfume oils, dimethylisosorbitol and cyclodextrins; fiber structure improving active substances (mono-, di- and oligosaccharides, glucose, maleic acid and lactic acid); defoamers such as silicones (dimethicon); dyes for dyeing the agent; anti-dandruff active substances (Piroctone Olamine, Zinc Omadine and Climbazol); light protective agents (derivatized benzophenones, cinnamic acid derivatives and triazine); active substances (pantolactone, allantoin, pyrrolidinone carboxylic acids and salts as well as bisabolol thereof); vitamins, provitamins and vitamin precursors, in particular those of the groups A, $B_3$, $B_5$, $B_6$, C, E, F and H; vegetal extracts (extracts of green tea, oak bark, stinging nettle, hamamelis, hops, henna, camomile, burdock root, field horsetail, hawthorn, linden blossom, almonds, aloe vera, spruce needles, horse chestnut, sandal wood, juniper, coconut, pomegranate, mango, apricot, lime, wheat, kiwi, melon, orange, grapefruit, elder, sage, rosemary, birch, mallow, lady's smock, rooibos, quendel, common yarrow, thyme, lemon balm, rest-harrow, coltsfoot, vanilla, marshmallow (althaea), meristem, ginseng and ginger); vegetal oils (macadamia nut oil, candle nut oil, palm oil, amaranth seed oil, peach stone oil, avocado oil, olive oil, cocoa oil, rape seed oil, sesame oil, jojoba oil, soja oil, peanut oil, evening primrose oil and tea tree oil); cholesterol; texturizers (sugar esters, polyol esters or polyol alkyl ethers); fats and waxes (fatty alcohols, beeswax, montan wax and paraffins); swelling and penetration substances (glycerin, propylene glycol monoethyl ether, carbonates, hydrogen carbonates, guanidines, ureas as well as primary, secondary and tertiary phosphates); opacifiers (latex, styrene/PVP copolymers and styrene/acrylamide copolymers); pearlizers (ethylene glycol mono and distearate as well as PEG-3-distearate); blowing agents such as propane-butane mixtures, $N_2O$, dimethyl ether, $CO_2$ and air; antioxidants.

One skilled in the art chooses these additional materials based on the desired properties of the preparations. The inventively used preparations preferably comprise additional active substances, auxiliaries and additives in amounts of 0.01 to 25 wt %, especially 0.05 to 15 wt %, based on total amount of the ready-for-use agent.

The ready-for-use lightening agent is applied onto the keratinic fibers and left on the fibers, particularly in hair, for a specified contact time. The preparation is usually applied by hand by the user. In this regard, personal protective clothing is preferably worn, especially protective gloves made, for example, of plastic or latex (disposable gloves). However it is also possible to apply the preparation onto the keratinic fibers with an application aid. The application and contact time temperature for the preparation is from room temperature to 45° C. The action of the preparation can optionally be intensified by use of an external heat supply such as a heating hood.

The preferred duration of treatment of the preparation on the keratinic fibers is 10 to 60 minutes, preferably 15 to 45 minutes. At the end of the treatment period, the remaining agent is washed out of the keratinic fibers with the help of a cleaning preparation or water. Once washed out, the keratinic fibers are optionally dried with a towel or with a hot air blower. There is no need to subsequently wash the hair with a shampoo if a strong surfactant-containing carrier was used.

A second subject matter of the present invention is a multi component packaging units (Kit-of-Parts) comprising at least a first container (C1) having a preparation (A) comprising in a cosmetic carrier a) at least one acylpyridinium derivative of Formula (I)

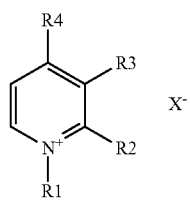

wherein

R1 is a $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a carboxy $C_2$-$C_6$ alkyl group, an aryl $C_1$-$C_6$ alkyl group, a heteroaryl $C_1$-$C_6$ alkyl group, an aryl group or a heteroaryl group, R2, R3 and R4 each independently of one another is hydrogen, a $C_1$-$C_6$ alkyl group, a halogen atom or a $C_1$-$C_6$ acyl group, with the proviso that at least one of the R2, R3 and R4 groups is a $C_1$-$C_6$ acyl group, and $X^-$ is a physiologically acceptable anion, and b) at least one hydroxyl group-containing amino acid and/or its physiologically acceptable salts and/or its alkyl esters, and at least one second container (C2) having a preparation (B) comprising in a cosmetic carrier at least one oxidizing agent.

The term "container" herein is a holder, independently of its shape, material or closure, which is capable of containing substances or mixtures of substances. Consequently, the term "container" includes but is not limited to the interior of a tube, a pouch or bag, a canister, a can, a pan, a bottle, a glass or a packet, a carton, a box, an envelope or other containers. The components of the lightening preparation can be present in a single container, although it is also possible and where appropriate, to separate them in various containers, and to instruct the consumer to mix them together before use.

In a particularly preferred embodiment, the packaging unit comprises at least one additional component chosen from personal protective clothing such as disposable gloves, apron, application aid such as comb, brush, paint brush or applicette, and instructions for use. In particular, the instructions for use contain information and directions for the consumer for using the agent from the containers of the packaging unit in a process according to the first subject matter of the invention. An applicette refers to a wide pencil whose shaft ends in a tip that facilitates and enables the fiber bundles or meshes to be divided from the totality of fibers.

The ready for use lightening agent is produced by blending preparation (A) with oxidizing preparation (B) of the kit of parts.

Preferred embodiments of the first subject matter of the invention apply mutatis mutandis for the inventive kit of parts of the second subject matter of the invention.

A third subject matter of the invention is a method for improving the lightening power of lightening agents and/or coloring agents for keratinic fibers, especially human hair, using an agent according to the first subject matter of the invention.

Finally, a further subject matter of the present invention is a method in which the agent of the first subject matter of the invention is produced by blending a preparation (A) comprising in a cosmetic carrier a) at least one acylpyridinium derivative of Formula (I)

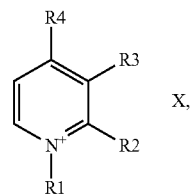

wherein

R1 is a $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a carboxy $C_2$-$C_6$ alkyl group, an aryl $C_1$-$C_6$ alkyl group, a heteroaryl $C_1$-$C_6$ alkyl group, an aryl group or a heteroaryl group, R2, R3 and R4 each independently of one another is hydrogen, a $C_1$-$C_6$ alkyl group, a halogen atom or a $C_1$-$C_6$ acyl group, with the proviso that at least one of the R2, R3 and R4 groups is a $C_1$-$C_6$ acyl group, and $X^-$ is a physiologically acceptable anion, and b) at least one hydroxyl group-containing amino acid and/or its physiologically acceptable salts and/or its alkyl esters, and at least one preparation (B) comprising in a cosmetic carrier at least one oxidizing agent, wherein the blended agent is immediately applied onto human hair, left on the fibers for a duration of time, and the remaining agent then rinsed out of the hair.

In the inventive method, the duration of the application of the agent ranges from 10 to 60 minutes, preferably 15 to 45 minutes, during which the agent is left on the fiber. The application temperature and the temperature during the contact period of the preparation is from room temperature to 45° C. In particular, the temperature is from 10° C. to 45° C., particularly 20° C. to 38° C. The action of the preparation can optionally be intensified by use of an external heat supply such as a heating hood.

At the end of the treatment period, the remaining agent is washed out of the keratinic fibers with the help of a cleaning preparation or water. Once washed out, the keratinic fibers are optionally dried with a towel or with a hot air blower. There is no need to subsequently wash the hair with a shampoo if a strong surfactant-containing carrier was used.

Regarding further preferred embodiments of the method according to the invention or of the use according to the invention, the statement made concerning the agents according to the invention applies mutatis mutandis. The following examples are intended to illustrate preferred embodiments of the invention without however limiting it thereto.

EXAMPLES

1. Synthesis Examples 1.1 Synthesis of 4-acetyl-1-methylpyridinium p-toluene sulfonate

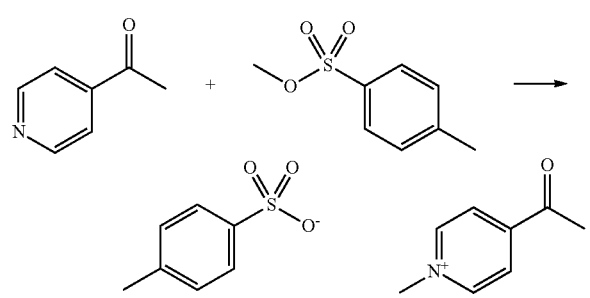

4-Acetylpyridine (30.0 g, 0.25 mol) and p-toluene sulfonic acid methyl ester (55.8 g, 0.30 mol) in 500 ml ethanol were heated under reflux for 5 hours. The solvent was removed under vacuum in a rotary evaporator and the residue was taken up in ether. After separating off the ether phase, the product slowly crystallized out. The product was dried under vacuum.

Yield: 59.9 g (82.5%)

$^1$H-NMR (400 MHz, DMSO-$d_6$): δ [ppm]=2.26 (s, 3H); 2.72 (s, 3H); 3.39 (s, 3H); 7.11 (d, 2H); 7.49 (d, 2H); 8.42 (d, 2H); 9.20 (d, 2H).

$^{13}$C-NMR (400 MHz, DMSO-$d_6$): δ [ppm]=20.8; 26.4; 48.1; 124.8; 125.3; 127.7; 138.9; 145.2; 146.5; 148.3; 195.8.

2. Blonding Example 2.1 Preparation of a Blonding Cream

Blonding creams were produced from the following listed ingredients:

| Raw material wt % | V1 | V2 | E |
|---|---|---|---|
| Hydrenol ® D [1] | 6.9 | 6.9 | 6.9 |
| Lorol ® techn. [2] | 2.5 | 2.5 | 2.5 |
| Eumulgin B1 [3] | 0.6 | 0.6 | 0.6 |
| Eumulgin B2 [4] | 0.6 | 0.6 | 0.6 |
| Akypo ® Soft 45 NV [5] | 10.0 | 10.0 | 10.0 |
| Plantacare ® 1200 UP [6] | 2.0 | 2.0 | 2.0 |
| Texapon ® K 14 S 70 C [7] | 2.8 | 2.8 | 2.8 |
| Ammonium sulfate | 1.0 | 1.0 | 1.0 |
| Ascorbic acid | 0.1 | 0.1 | 0.1 |
| Sodium silicate 40/42 [8] | 0.5 | 0.5 | 0.5 |
| Turpinal ® SL [9] | 0.2 | 0.2 | 0.2 |
| Potassium hydroxide | 0.8 | 0.8 | 0.8 |
| Ammonia (25% conc. solution) | 7.1 | 7.1 | 7.1 |
| L-Serine | — | — | 2.0 |
| 4-Acetyl-1-methylpyridinium p-toluene sulfonate | — | 2.0 | 2.0 |
| Water | ad 100 | ad 100 | ad 100 |

[1] Hydrenol ® D INCI name: Cetearyl alcohol (Cognis)
[2] Lorol ® tech. INCI name: Coconut alcohol (Cognis)
[3] Eumulgin ® B1 INCI name: Ceteareth-12 (Cognis)
[4] Eumulgin ® B2 INCI name: Ceteareth-20 (Cognis)
[5] Akypo ® Soft 45NV INCI name: Sodium Laureth-5 carboxylate (KAO Chemicals)
[6] Plantacare ® 1200 UP INCI name: Lauryl Glucoside (Cognis)
[7] Texapon ® K 14 S 70 C INCI name: Sodium Myreth Sulfate (ca. 70% active substance); (Cognis)
[8] Sodium silicate 40/42 Soda-water glass
[9] Turpinal ® SL (ca. 60% INCI name: Etidronic Acid, Aqua active substance content); (Solutia)

The fat components were melted together at 80° C. and dispersed with part of the water. The remaining components of the formulation were then successively incorporated with stirring. Water was then added to make up 100% and the formulation was stirred without heating. The formulation V1 is a non-inventive blonding formulation without any added activator. The formulation V2 is likewise a non-inventive comparative formulation that contains solely a cationic 4-acetylpyridinium derivative. The formulation E is an inventive formulation.

2.2 Blending with the Developer Dispersion

Each blonding cream was mixed up in the ratio 1:1 with one of the following formulated developer dispersions. The pH of the application mixture was from 9 to 10.2.

| Raw material | wt % |
|---|---|
| Ammonia 25% | 0.62 |
| Dipicolinic acid | 0.10 |
| Disodium pyrophosphate | 0.03 |
| Turpinal ® SL [9] | 1.50 |
| Texapon ® NSO [10] | 2.00 |

-continued

| Raw material | wt % |
|---|---|
| Dow Corning ® DB 110 A [11] | 0.07 |
| Aculyn ® 33A [12] | 12.00 |
| Hydrogen peroxide, 50% | 22.40 |
| Water | ad 100 |

[10] Texapon ® NSO (ca. 27.5% active substance); INCI name: Sodium Laureth Sulfate (Cognis)
[11] Dow Corning ® DB 110 A INCI name: Dimethicon (Dow Corning)
[12] Aculyn ® 33 (ca. 28% solids in water); INCI name: Acrylates Copolymer (Rohm & Haas)

For the blonding process, strands of dark brown hair (Code Kerling 2/0), weighing ca. 0.7 g were treated with four times the amount of the premixed application mixture. After the strands had been blonded for 30 minutes at 32° C. they were washed with a conventional shampoo and dried with a hair dryer.

2.3 Evaluation of the Lightening Power

Each strand of hair was measured colorimetrically before and after the bleaching process. The ΔL-value according to the following equation was taken as a measure for the lightening power of each formulation:

$\Delta L = L_{after} - L_{before}$ $L_{after}$ = lightness of the strands after bleaching
$L_{before}$ = lightness of the strands before bleaching Twelve determinations were made for each formulation, an average value being determined from each single value. The greater the ΔL-value, the better is the lightening power of the formulation.

| Lightening power for dark brown strands (Kerling 2/0) | | |
|---|---|---|
| ΔL (V1) | ΔL (V2) | ΔL (E) |
| 5.4 | 6.0 | 6.8 |

2.4 Interpretation of the Results

An estimation of the bleaching actions of the different formulations can be made by comparing the ΔL values. It is clearly evident that significantly higher ΔL values—and hence a better lightening—could be achieved with the inventive combination, than was possible by adding hydrogen peroxide alone or in combination with the acylpyridinium derivative. Consequently, a significant improvement over the existing prior art could be achieved by adding this specific combination of three components.

We claim:

1. Agent for treating keratinic fibers comprising in a cosmetic carrier:
   (i) at least one oxidizing agent,
   (ii) at least one acylpyridinium derivative of Formula (I)

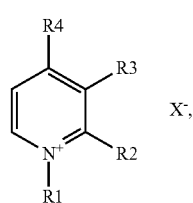

(I)

wherein
   R1 is a $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a carboxy $C_2$-$C_6$ alkyl group, an aryl $C_1$-$C_6$ alkyl group, a heteroaryl $C_1$-$C_6$ alkyl group, an aryl group or a heteroaryl group,
   R2, R3 and R4, each independently of one another, is hydrogen, a $C_1$-$C_6$ alkyl group, a halogen atom or a $C_1$-$C_6$ acyl group, with the proviso that at least one of the R2, R3 and R4 groups stands for a $C_1$-$C_6$ acyl group, and
   X⁻ is a physiologically acceptable anion, and
   (iii) at least one hydroxyl group-containing amino acid and/or physiologically acceptable salts and/or alkyl esters thereof.

2. Agent according to claim 1 wherein the acylpyridinium derivative of Formula (I) is at least a compound in which either R2 or R4 is a $C_1$-$C_6$ acyl group.

3. Agent according to claim 2 wherein the acylpyridinium derivative of Formula (I) is at least a compound in which either R2 or R4 is an acetyl group.

4. Agent according to claim 1 wherein the acylpyridinium derivative of Formula (I) is at least a compound chosen from 4-acetyl-1-methylpyridinium p-toluene sulfonate, 4-acetyl-1-methylpyridinium benzene sulfonate, 4-acetyl-1-methylpyridinium hydrogen sulfate, 4-acetyl-1-methylpyridinium acetate, 4-acetyl-1-allylpyridinium p-toluene sulfonate, 4-acetyl-1-allylpyridinium benzene sulfonate, 4-acetyl-1-allylpyridinium hydrogen sulfate, 4-acetyl-1-allylpyridinium acetate, 2-acetyl-1-methylpyridinium p-toluene sulfonate, 2-acetyl-1-methylpyridinium benzene sulfonate, 2-acetyl-1-methylpyridinium hydrogen sulfate, 2-acetyl-1-methylpyridinium acetate, 2-acetyl-1-allylpyridinium p-toluene sulfonate, 2-acetyl-1-allylpyridinium benzene sulfonate, 2-acetyl-1-allylpyridinium hydrogen sulfate and 2-acetyl-1-allylpyridinium acetate.

5. Agent according to claim 1 wherein the acylpyridinium derivative of Formula (I) is present in an amount of 0.001 to 15 wt %, based on total weight of the ready-for-use agent.

6. Agent according to claim 1 wherein the at least one oxidizing agent is at least a compound chosen from hydrogen peroxide, alkali metal peroxides and/or alkali metal perborates.

7. Agent according to claim 6 wherein the at least one oxidizing agent is hydrogen peroxide.

8. Agent according to claim 1 wherein the at least one hydroxyl group-containing amino acid is a compound chosen from serine, tyrosine, threonine, 4-hydroxyproline and/or methyl or ethyl esters and/or physiologically acceptable salts thereof.

9. Agent according to claim 8 wherein the at least one hydroxyl group-containing amino acid is L-serine.

10. Agent according to claim 1 wherein the at least one hydroxyl group-containing amino acids and/or salts and/or alkyl esters is present in an amount of 0.01 to 10 wt %, based on total weight of the ready-for-use agent.

11. Multi component packaging unit comprising:
   a first container (C1) having a preparation (A) comprising in a cosmetic carrier a) at least one acylpyridinium derivative of Formula (I)

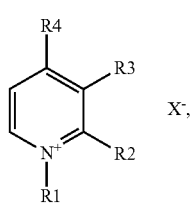

(I)

in which
R1 is a $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a carboxy $C_2$-$C_6$ alkyl group, an aryl $C_1$-$C_6$ alkyl group, a heteroaryl $C_1$-$C_6$ alkyl group, an aryl group or a heteroaryl group, R2, R3 and R4, each independently of one another, is hydrogen, a $C_1$-$C_6$ alkyl group, a halogen atom or a $C_1$-$C_6$ acyl group, with the proviso that at least one of R2, R3 and R4 is a $C_1$-$C_6$ acyl group, and $X^-$ is a physiologically acceptable anion, and b) at least one hydroxyl group-containing amino acid and/or physiologically acceptable salts and/or alkyl esters thereof, and a second container (C2) having a preparation (B) comprising in a cosmetic carrier at least one oxidizing agent.

12. Method of lightening and/or coloring keratinic fibers comprising the steps of:
preparing an agent for treating keratinic fibers by mixing a preparation (A) comprising in a cosmetic carrier a) at least one acylpyridinium derivative of Formula (I)

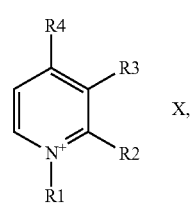

(I)

wherein
R1 is a $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a carboxy $C_2$-$C_6$ alkyl group, an aryl $C_1$-$C_6$ alkyl group, a heteroaryl $C_1$-$C_6$ alkyl group, an aryl group or a heteroaryl group, R2, R3 and R4, each independently of one another, is hydrogen, a $C_1$-$C_6$ alkyl group, a halogen atom or a $C_1$-$C_6$ acyl group, with the proviso that at least one of R2, R3 and R4 is a $C_1$-$C_6$ acyl group, and $X^-$ is a physiologically acceptable anion, and b) at least one hydroxyl group-containing amino acid and/or physiologically acceptable salts and/or alkyl esters thereof, together with a preparation (B) comprising in a cosmetic carrier at least one oxidizing agent,
applying the agent onto the keratinic fibers,
leaving the agent on the fibers for a time, and
rinsing the remaining agent out of the fibers.

* * * * *